United States Patent [19]

Jousson

[11] Patent Number: 4,907,744

[45] Date of Patent: Mar. 13, 1990

[54] ORAL HYGIENE DEVICE

[75] Inventor: Pierre-Jean Jousson, Geneva, Switzerland

[73] Assignee: Les Produits Associes LPA-Broxo S.A., Switzerland

[21] Appl. No.: 189,668

[22] Filed: May 3, 1988

[51] Int. Cl.$^4$ ............................................. A61C 17/02
[52] U.S. Cl. ...................................... 239/449; 239/447; 239/552; 239/586; 137/625.44; 137/625.48; 137/872; 137/875; 137/901
[58] Field of Search .................. 137/901, 872, 625.48, 137/625.44, 875; 239/586, 443, 436, 444, 446–449, 552; 128/66

[56] References Cited

U.S. PATENT DOCUMENTS

| 904,662 | 11/1908 | Wells | 137/901 |
|---|---|---|---|
| 2,286,933 | 6/1942 | Royal | 239/446 |
| 3,802,563 | 4/1974 | Sasaki et al. | 137/625.48 |
| 3,986,523 | 10/1976 | Pacht | 239/443 |
| 4,138,064 | 2/1979 | Moret | 239/582.1 |
| 4,489,712 | 12/1984 | Ohshima | 137/625.48 |
| 4,502,508 | 3/1985 | Lester | 137/625.48 |
| 4,671,259 | 6/1987 | Kirchner | 128/66 |
| 4,718,457 | 1/1988 | Luger | 137/875 |

FOREIGN PATENT DOCUMENTS 3044025 6/1982 Fed. Rep. of Germany .

Primary Examiner—Andres Kashnikow
Assistant Examiner—Christopher G. Trainor
Attorney, Agent, or Firm—Kane, Dalsimer, Sullivan, Kurucz, Levy, Eisele and Richard

[57] ABSTRACT

The oral hygiene device comprises a nozzle-holder connectable to a liquid source and a nozzle (1) removably attached to the nozzle-holder, the nozzle being intended for spraying either a multi-jet of liquid via a first duct or a single jet of liquid via a second duct. A two-way valve (5) makes it possible to direct the liquid towards one duct or the other and therefore the branching of the two liquid ducts are located in the nozzle itself. There is a restoring spring (27) which is such that the stable position of the device is for multi-jet spraying, while under the action of an external force exerted on the control member (6) of the valve the device assumes the single-jet position.

13 Claims, 5 Drawing Sheets

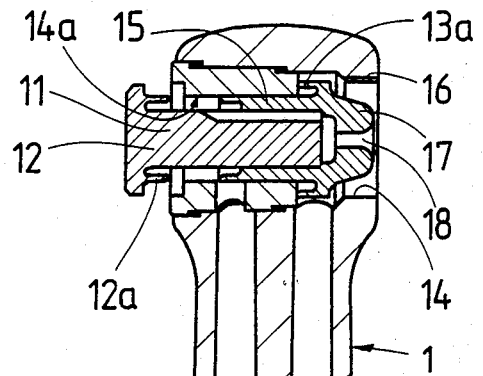
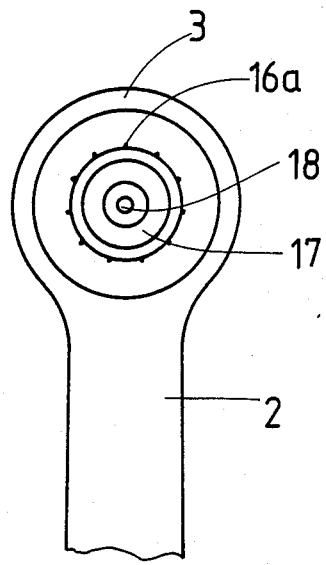
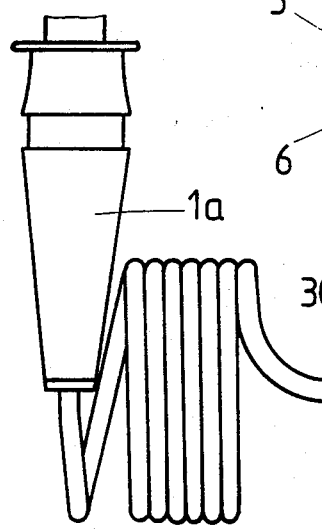
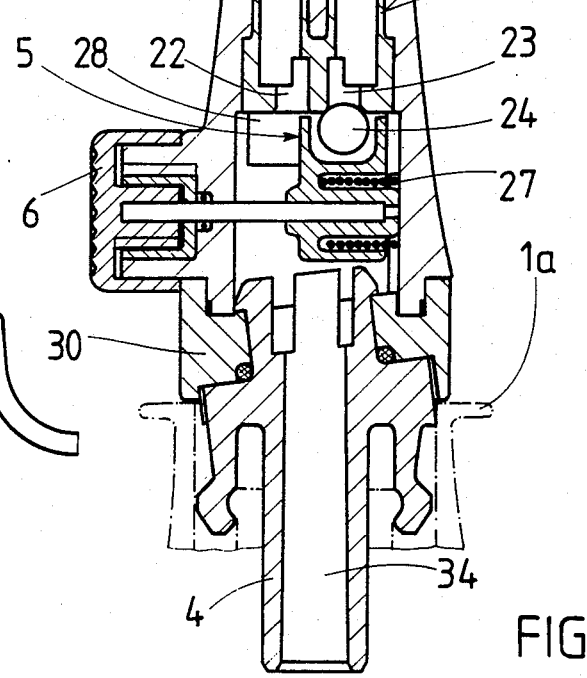

ORAL HYGIENE DEVICE

FIELD OF THE INVENTION

The present invention relates to an oral hygiene device comprising a nozzle-holder connectable to a liquid source and a nozzle attached removably to the nozzle-holder, this nozzle having, in its head, a series of holes forming the outlet orifices of a first liquid duct and allowing the emission of a multi-jet of liquid, and a single hole forming the outlet orifice of a second liquid duct and allowing the emission of a single jet of liquid, a two-way valve being provided, controlled by a control member so as to direct the liquid either into the first duct or into the second duct.

PRIOR ART

Such a device is known, for example, from German Patent No. 3,044,025. Here, the control valve and therefore the branching of the two ducts are located in the nozzle-holder. This makes the components more complicated to produce and requires not only a special nozzle, but also a special nozzle-holder. Furthermore, during the mounting of the nozzle on the nozzle-holder, the two conduits which open out at the lower end of the nozzle have to be connected to those opening out at the upper end of the nozzle-holder, this requiring some care to ensure that the two ducts are connected correctly. Another disadvantage is that, when the appliance is put into operation, the spray nozzle can equally be either in the multi-jet spray position or in the single-jet spray position, and if the appliance is in the latter position this is a danger to the gums which risk receiving too powerful a jet which could injure them.

SUMMARY OF THE INVENTION

The present invention proposes to provide a device of simpler construction which avoids the above-mentioned disadvantages and which requires the connection of only one duct.

To achieve this, the device according to the invention is defined in that the said valve and therefore the branching of the two liquid ducts are located in the nozzle itself, and the valve is subjected to the action of a restoring spring which is such that the stable position of the device is for multi-jet spraying, whilst under the action of an external force exerted on the control member counter to the action of the spring, the device assumes the single-jet spray position.

This device has many advantages in relation to the known device. It is of simple construction and allows the nozzle to be connected to the nozzle-holder easily without the previous positioning of the two parts, because only a single duct, in this particular case a central duct, has to be connected. Since the valve forms part of the nozzle, it can easily be replaced. Another important advantage is with regard to the user's safety because, since the valve is always in the multi-jet spray position, this avoids any traumatizing action on the gums when the appliance is put into operation. Only as a result of deliberate actuation of the control member is the nozzle put into the single-jet position.

The valve is preferably a ball valve, as defined in claim 2. It is simple and easy to manipulate, and there is no risk of jamming under the effect of a change in temperature of the liquid or the like.

On the other hand, the control member is preferably installed on the body of the nozzle, and with this embodiment the nozzle can be fitted to and used with existing appliances having a single-duct nozzle-holder, without these being modified.

The axis of the single jet must be as near as possible to the axis of the multi-jet, so that the treated spot remains the same during the changeover. For this reason, according to a preferred form of the invention, the nozzle head is designed so that the multi-jet orifices are arranged along a circle and the single-jet orifice is the center of this circle. This arrangement also makes it possible to reduce the dimensions of the part located in the mouth.

Other aspects of the invention emerge from the claims.

BRIEF DESCRIPTION OF THE DRAWINGS

The invention will be understood clearly from the following description of an exemplary embodiment and of some alternative versions, which is made with reference to the accompanying drawings in which:

FIG. 2 shows the same view as FIG. 1 with the nozzle head in the unclogging position and the valve in the single-jet position with a part of a nozzle holder shown in phantom.

FIG. 2A is a fragmentary elevational view of a nozzle holder;

FIG. 3 is a front view of the nozzle head, showing the jet orifices.

DESCRIPTION OF THE PREFERRED EMBODIMENTS

Figure 1:
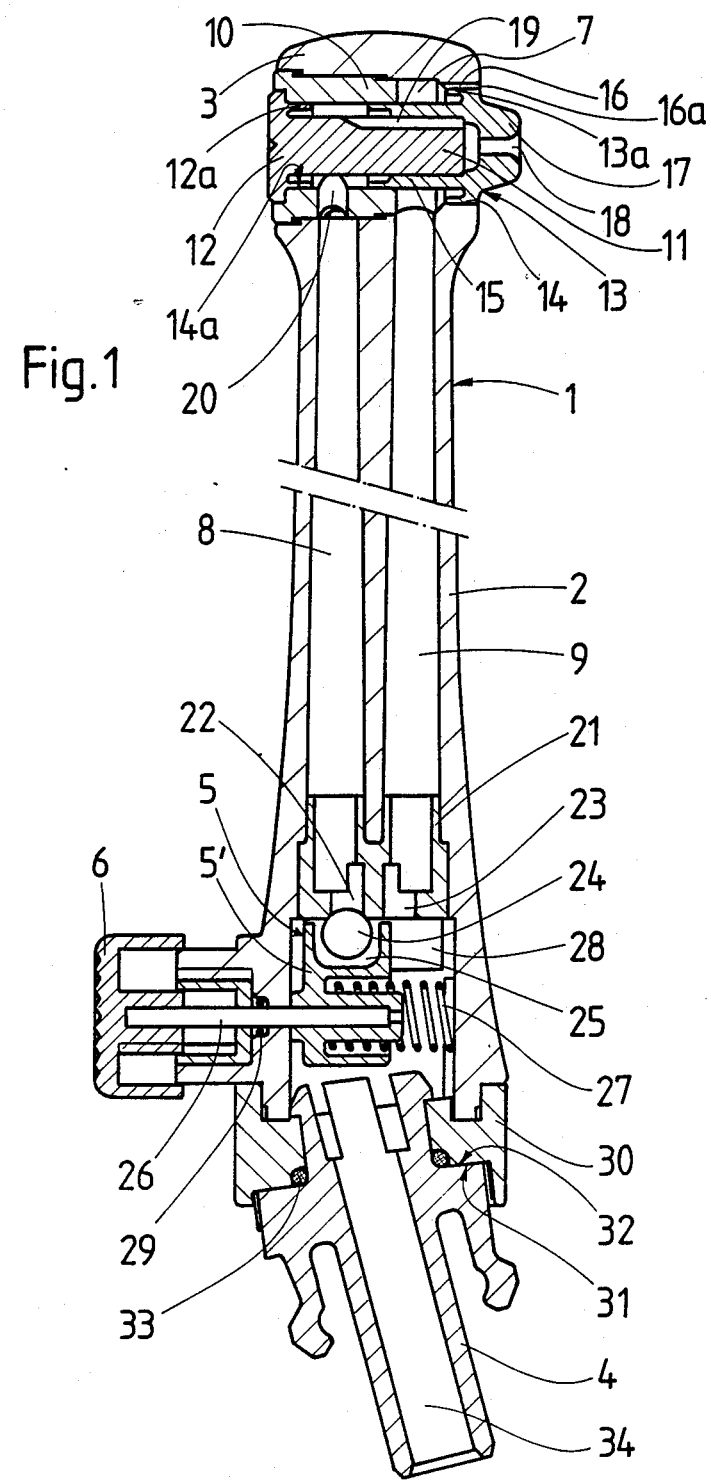
FIG. 1 is a view in elevation and in longitudinal section of the nozzle with the nozzlehead and the valve in the multi-jet spray position.

The device illustrated in FIGS. 1 to 3 comprises a nozzle composed of a nozzle body 2, the front end of which forms the nozzle head 3, whilst its rear end is equipped with a piece 4 for connection to the nozzle-holder 1a containing the means for feeding the nozzle via the duct 34. A valve 5 controlled by means of a pushbutton 6 and located near the rear end of the body 2 of the nozzle 1 makes it possible to adjust the flow of fluid inside the nozzle.

The hemispherical nozzle head 3 is provided with an axial bore 7 opening onto the front face in a circular aperture 14 of reduced diameter and onto the rear face in another circular aperture 14a of widened diameter, this bore 7 being in communication with two feed ducts 8 and 9 arranged parallel to one another in the nozzle body 2. Fastened, for example by ultrasonic welding, in the rear part of the axial bore 7 is a distribution bushing 10, in which a cylindrical retaining pin 11 is mounted under firm friction. The rear part of this pin 11 forms a head 12 equipped with a part of reduced diameter 12a which, in the spray position illustrated in FIG. 1, engages under firm friction inside the distribution bushing 10. The front part of the pin 11 is driven into a spray pin 13 which, in the spray position, is intended to engage into the cylindrical aperture 14. This spray pin 13 has a hollow cylindrical part which receives the retaining pin 11 and the outside diameter of which corresponds to the diameter of the part 12a of the head 12. The length of this hollow cylindrical part 15 is such that, either in the spray position illustrated in FIG. 1 or in the unclogging position illustrated in FIG. 2 and explained later, it engages under firm friction into the distribution bushing 10. On the same side as the aperture 14 in the head 3, the spray pin 13 possesses a bearing surface 13a, the diameter of which corresponds to that of the aperture 14 and which, in the spray position, engages under firm friction inside the said aperture 14. The periphery of the latter is provided with several axial grooves 16 which, when the spray pin 13 is engaged in the aperture 14, defines several small apertures 16a, through which the liquid can pass in the multi-jet position. With this configuration, a multi-jet with parallel jets is obtained. The spray pin 13 terminates on the front face in a boss 17 having a small central orifice 18, through which the liquid passes in the single-jet position. Thus, the multi-jet apertures 16a and the single-jet orifice 18 are concentric, as illustrated in FIG. 3, and the jets emitted are parallel.

Alternatively, the retaining pin 11 and the spray pin 13 could be in one piece, two pieces having been chosen for the sake of convenience of manufacture. Moreover, the axial grooves 16 forming the multi-jet orifices could also be made on the periphery of the bearing surface 13a of the spray pin 13.

In the spray position illustrated in FIG. 1, the single-jet aperture 18 is put in communication with the first feed duct 8 via several axial grooves 19, which the retaining pin 11 possesses over some of its length, and an orifice 20 located in the distribution bushing 10 and placed opposite the feed duct 8. In this same spray position, the multi-jet apertures 16a are put in communication with the second feed duct 9 via an annular free space of the bore 7 which surrounds the inner part of the spray pin 13 and into which the duct 9 opens directly.

The arrival of the liquid at one or other of the feed ducts 8 and 9 is controlled by the ball valve 5 placed in the rear part of the nozzle 1. Mounted inside the body 2 of the nozzle is a distributor seat 21 provided with two inlet ports 22, 23, one 22 communicating with the duct 8 for feeding the single jet and the other 23 communicating with the duct 9 for feeding the multi-jet. The respective entrances of these ports form two seats for a ball 24 which is mounted freely in a lateral receptacle 25 of a cage 5'. This cage 5' can shift in a distribution chamber 28 located in the nozzle body 2 and in communication with the liquid intake duct 34, and it is actuated by means of a rod 26 fixed to the pushbutton 6. The latter is pushed by a spring 27 which is accommodated in the chamber 28 and which normally keeps it in the position of rest, indicated in FIG. 1, in which the multi-jet duct 9 is open, whilst under the action of the pressure of the liquid the ball 24 closes the single-jet feed duct 8. The choice of the multi-jet position as the normal position of the appliance was made so as to avoid any accidental traumatism of the gums.

Pressure exerted on the pushbutton 6 causes the cage 5' to shift in the chamber 28 counter to the restoring spring 27, up to the position indicated in FIG. 2, in which the inlet port 23 of the multi-jet duct is closed by means of the ball 24 which is pressed against the port 23 as a result of the pressure of the water, and the single-jet inlet port 22 is opened. It is therefore only as a result of actuation on the pushbutton 6 that the single jet is obtained. As long as the user presses the button 6, the appliance works in the single-jet mode, but as soon as he releases the pressure on the button 6 the spring 27 returns the valve to the normal positio for the appliance to work in the multi-jet mode, driving along with it, in its travel, the cage 5' and the ball 24 which will be laid against the port 22 under the action of the pressure of the water in the chamber 28. An O-ring seal 29 ensures the sealing of the rod 26 of the valve 5.

During the interval of time necessary to change from the multi-jet position to the single-jet position, and vice versa, the two orifices discharge, but since there is a double discharge the spraying force is low, and because of this there is virtually no risk of traumatism.

In the spray position illustrated in FIG. 1, the spray pin 13 and retaining pin 11 are therefore fitted in the nozzle head 3 under firm friction, on the one hand the part 12a of the retaining pin 11 engaging into the distribution bushing 10 and on the other hand the bearing surface 13a of the spray pin 13 engaging into the aperture 14. This position is obtained as a result of external pressure exerted by one of the user's fingers on the head 12 of the retaining pin 11.

In this position, the user can choose between multi-jet spraying or single-jet spraying by acting on the button 6, as explained.

To ensure that the outlet orifices of the nozzle, especially the multi-jet outlet orifices 16a which are of very small size, do not become clogged either as a result of impurities or as a result of the limestone contained in the water, there is an "unclogging" position illustrated in FIG. 2. This position is obtained as a result of pressure exerted by the user's finger on the boss 17 of the spray pin 13, until the head 12 of the retaining pin 11 is released from the distribution bush 10 and the bearing surface 13a of the spray pin 13 comes away from the grooves 16.

In this unclogging position, the button 6 can equally be in one position or the other and the pressure of the water drives the impurities outwards on one side or the other of the bore 7 in the nozzle head 3. In this position, the retaining pin 11 and the spray pin 13 are still retained under firm friction in the distribution bush 10, thus preventing them from shifting in the bore 7 under the effect of the water pressure.

The best possible massaging result in the multi-jet position is obtained when the nozzle is a few millimeters from the gum, and the central boss makes it possible to determine the appropriate distance, for example 2 to 3 millimeters. This boss also prevents the orifices from being damaged as a result of friction against the teeth.

Moreover, for ergonomic purposes, the nozzle 1 can be arranged in the axis of the connection piece (FIG. 2), hence in the axis of the nozzle-holder (not shown), or can form a small angle of, for example, 15° relative to this axis simply as a result of the rotation of the nozzle 1 relative to the connection piece 4 (FIG. 1). To this end, between the connection piece 4 and the body 2 of the nozzle there is a retaining bushing 30 which is welded ultrasonically to the rear end of the body 2 and the rear face 31 of which has an inclination of approximately 7.5° relative to the rear face of the nozzle, whilst the connection piece 4 has a bearing surface 32 likewise inclined at approximately 7.5° relative to the plane perpendicular to its longitudinal axis, so that, in the position illustrated in FIG. 2, the two inclinations compensate one another and the axis of the nozzle coincides with the axis of the connection piece 4 and consequently of the nozzle-holder, whereas, if the nozzle is rotated through 180° relative to the piece 4 for connection to the nozzle-holder to reach the position illutrated in FIG. 1, the two inclinations are added together and the axis of the nozzle is inclined at 15° relative to the axis of the nozzle-holder, an O-ring seal 33 ensuring sealing between the retaining bush 30 and the connection piece 4.

Other embodiments can be provided for the two-way valve, and several examples, also showing another possible alternative version of the nozzle head, will be described below.

Figure 4:
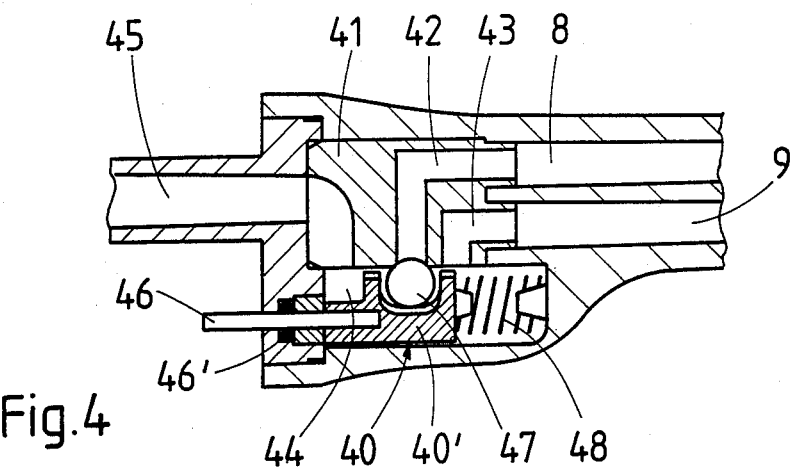
FIG. 4 is a view in elevation and longitudinal section of a second embodiment of the valve.

FIG. 4 relates to a slide valve 40 comprising a cage 40' which shifts in the distribution chamber 44 parallel to the axis of the ducts 8 and 9 and which is equipped with a ball 47. Two bent ducts 42, 43 pass through the distributor seat 41 and open, on the one hand, into the ducts 8 and 9 for feeding the nozzle and, on the other hand, into the distribution chamber 44 in communication with the feed duct 45 connected to the nozzle-holder. The valve is controlled by means of a rod 46 which is equipped with a sealing means 46' and which is itself controlled by means of a control bushing (not shown) mounted on the nozzle-holder. In the normal position of the appliance, a spring 48 mounted in the chamber 44 presses the valve 40 into the position shown in the Figure, in which the ball 47 closes the entrance of the single-jet feed duct 9 and consequently opens the multi-jet feed duct 8. It is clear that the rod 46 can be controlled by a button sliding on the body of the nozzle and executing a movement parallel to the axis of the nozzle.

Figure 5:
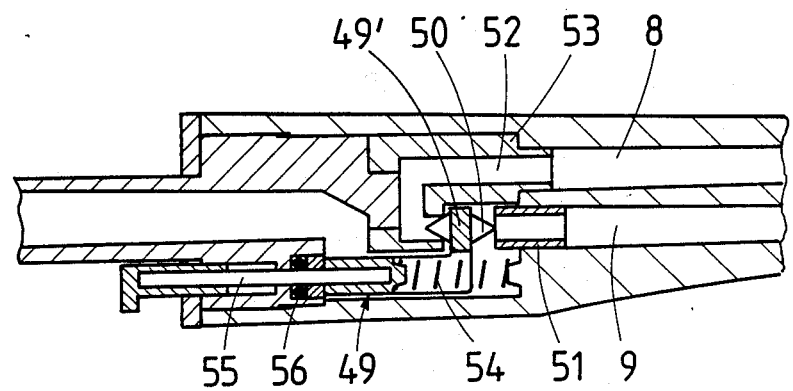
FIG. 5 shows the same view of a third embodiment of the valve.

The alternative version illustrated in FIG. 5 likewise relates to a slide valve 49 of reduced stroke, controlled by means of a nozzle-holder control bushing or by means of a button sliding on the nozzle body, by way of a control rod 55, an O-ring seal 56 ensuring sealing. In this case, the movable part 49' of the valve 49 is bent, and its end is equipped with a shut-off member 50 having opposing double faces intended for shutting off either the inlet port of the multi-jet feed conduit 9 via the connection 51 or the inlet port of the single-jet feed duct 8 opposite the other port, via the duct 52 passing through the distributor seat 53. As in the preceding embodiments, a spring 54 presses the movable part 49' of the valve into the position illustrated in FIG. 5, which is the multi-jet spray position.

Figure 6:
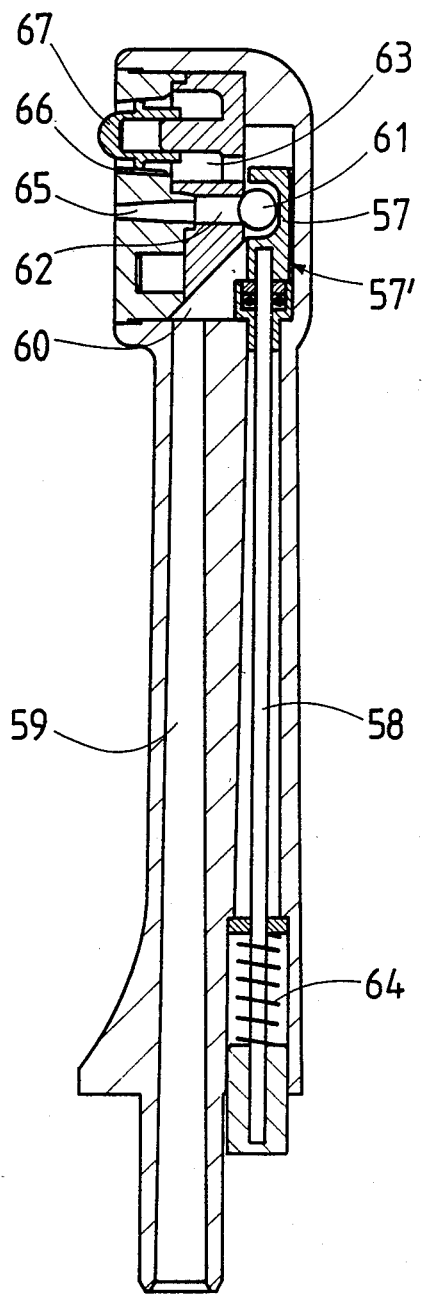
FIG. 6 is a view in longitudinal section of another embodiment of the nozzle, with the valve mounted in the head.
Figure 7:
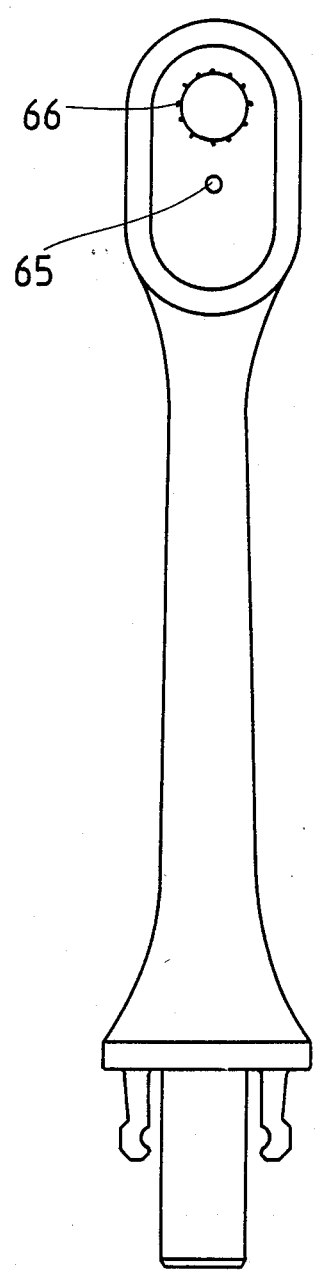
FIG. 7 is a front view of the nozzle illustrated in FIG. 6.

The embodiment shown in FIGS. 6 and 7 is somewhat different, since, here, the cage 57' of the valve 57 with a ball 61 is mounted in the head of the nozzle and is actuated by means of a rod 58 which is controlled either by means of a control bushing on the nozzle-holder or by means of a button sliding on the nozzle body, these not being shown. The nozzle body therefore has passing through it a single duct 59 opening into a distribution chamber 60 which is located in the head and which, depending on the position of the cage 57' in which the ball 61 is mounted freely, communicates either with the first duct 62 supplying the single jet or with the second duct 63 supplying the multi-jet. As in the preceding cases, a spring 64 presses the cage 57' constantly into the multi-jet spray position, as illustrated in FIG. 6. In this example, the form of the nozzle head differs from that illustrated in FIGS. 1 to 3, in that the single-jet outlet orifice 65 and the circle formed by the multi-jet outlet orifices 66 are not concentric, but are arranged next to one another. Of course, this embodiment of the nozzle can be equipped with the head having concentric single and multi-jets.

Figure 8:
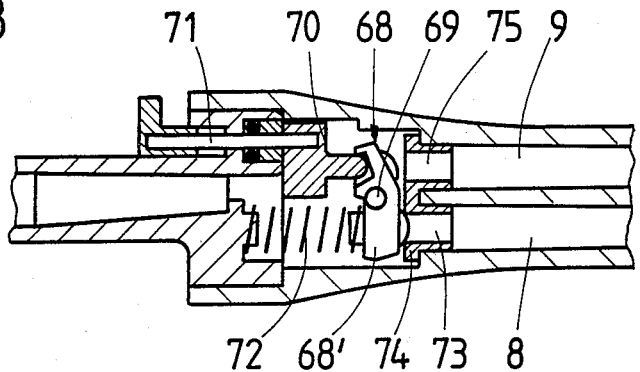
FIG. 8 is a view in longitudinal section of a fifth embodiment of the valve.

FIG. 8 shows a fifth possible embodiment of the valve 68, of which the movable part 68' here tilts about a pivot 69 and is actuated by means of a control piece 70 itself controlled by a rod 71. In the normal position of the appliance shown in the Figure, this movable part 68' is pressed by means of a spring 72 against the port 73 of the distributor seat 74 in communication with the single-jet feed duct 8, whilst it opens the port 75 in communication with the multi-jet feed duct 9.

Figure 9:
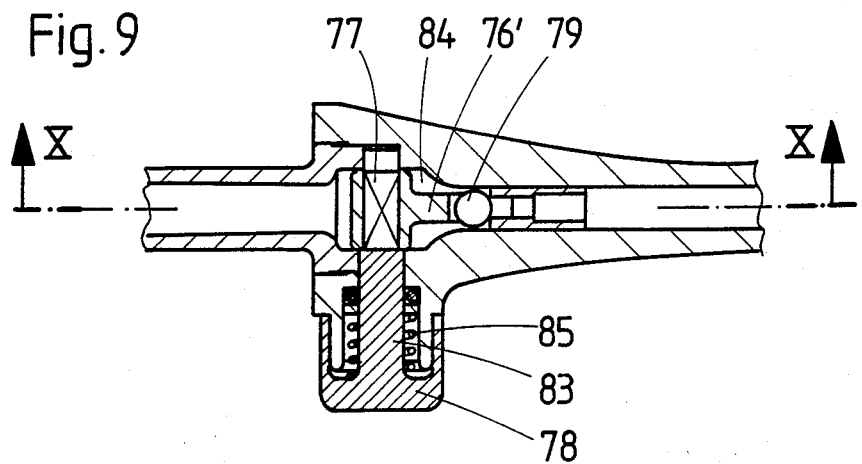
FIG. 9 is a view in longitudinal section of a sixth embodiment of the valve.
Figure 10:
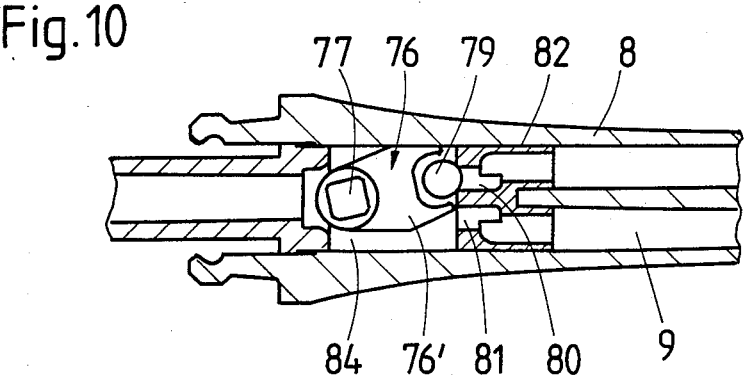
FIG. 10 is a sectional view in the X—X axis of FIG. 9.

The last alternative version illustrated in FIGS. 9 and 10 is that of a ball valve 76 with rotary control. The cage 76' holding the ball 79 is mounted on a square 77 fixed to a rotary control button 78 and can be tilted between two positions in the distribution chamber 84. In one of these positions, the ball 79 shuts off the inlet port 80 of the single-jet feed duct 8, whilst in the other position the inlet port 81 of the multi-jet feed duct 9 is closed, these inlet ports 80, 81 being formed in a distributor seat 82 mounted in the nozzle. A helical spring 85 surrounding the axle 83 of the control button 78 makes it possible to return the cage 76' into its normal position, in which the multi-jet orifice is opened.

Of course, the invention is not limited to the embodiments described and many other alternative forms are possible.

I claim:

1. An oral hygiene device comprising a nozzle-holder connectable to a liquid source and a nozzle removably attached to the nozzle-holder, the nozzle comprising a head having a series of holes forming outlet orifices of a first liquid duct and allowing emission of a multi-jet of liquid, and a single hole forming an outlet orifice of a second liquid duct and allowing emission of a single jet of liquid, a two-way valve being provided, controlled by a control member in order to direct the liquid either into the first duct or into the second duct, wherein the said valve (5, 40, 49, 57, 68, 76) and therefore branching of the two liquid ducts (8, 9, 62, 63) are located in the nozzle itself, and the valve is subjected to the action of a restoring spring (27, 48, 54, 64, 72, 85) which is such that the stable position of the device is for emitting the multi-jet of liquid, whilst under the action of an external force exerted on the control member counter to the action of the spring, the device emits the single-jet of liquid, the nozzle head (3) having a front face and a rear face and an axial bore (7) which opens onto the front face forming a front aperture and onto the rear face forming a rear aperture; a spray pin (11, 13) frictionally mounted in the bore (7), the spray pin (11, 13) having a front part and a rear part, the front part being part located in the zone of the front aperture (14), the front part having a boss (17) having the single-jet spray orifice located centrally therein (18) in communication with the second liquid ducts (8) and, the rear part being located in the zone of the rear aperture and having a shut-off piece (12), the rim of the said front aperture (14) and at least one of theperiphery of the front part of the pin being equipped with axial grooves (16) forming the multi-jet spray orifices (16a) in communication with the first liquid duct (9), said spray pin (11, 13) being shiftable between a first and a second position, in first position the rear part (12) of the pin (11, 13) is depressed into the bore (7) and closes the rear aperture (14a), the front part (13) of the pin being engaged in the front aperture (14), the single-jet spray orifice and the multi-jet spray orifices (16a) being operational, whilst in the second position said shut-off piece (12) is released rearwards under the effect of pressure exerted on the boss (17), and the spray pin (11, 13) is released from the apertures (14, 14a), thus freeing the axial grooves (16) and the rear aperture (14a).

2. A device as claimed in claim 1, wherein the nozzle includes a nozzle body and the valve is a ball valve (5, 40, 57, 76), the ball (24, 47, 61, 79) of which is held freely in a cage (5', 40', 57', 76') shiftable in a distribution chamber (28, 44, 60, 84) by means of the control member (6, 26; 46; 58; 78) in front of inlet ports forming seats (22, 23) of the first and the second ducts (8, 9; 62, 63), depending on the position of the said cage, the ball being pressed against one or other of these seats under the pressure of the liquid.

3. A device as claimed in claim 2, wherein the cage (76') is shiftable angularly about an axle (77), and wherein the control member is a rotary button (78).

4. A device as claimed in claim 2, wherein the cage (5') is shiftable in the nozzle body perpendicularly to the axis of the ducts (8, 9), and wherein the control member is a pushbutton (6) mounted on this nozzle body and connected to the said cage by means of a rod (26).

5. A device as claimed in claim 2, wherein the cage (40') is shiftable in the body of the nozzle parallel to the axis of the ducts (8, 9), the inlet ports of which are connected to two bent ducts (42, 43), and wherein the control member is a longitudinal rod (46).

6. A device as claimed in claim 2, wherein the cage (57') is shiftable in the head of the nozzle, the control member being a rod (58) passing through the nozzle body, and wherein the ball (61) is arranged so as to close either the inlet port of the duct (63) for the multi-jet (66) or the inlet port of the duct (62) for the single jet (65), the two ports being arranged side by side in the nozzle head.

7. A device as claimed in claim 1, wherein a movable part (49') of the valve (49) has, on two opposite sides, shut-off pieces (50) shiftable between two opposite inlet ports.

8. A device as claimed in claim 1, wherein a movable part of the valve (68) tilts about a pivot (69), one of its ends being subjected to the action of the restoring spring (72), whilst the other end is subjected to the action of the control member (70, 71).

9. A device as claimed in claim 4, wherein the control member is actuated by means of a button mounted on the nozzle.

10. A device as claimed in claim 4, wherein the control member is actuated by means of a a control bushing mounted on the nozzle-holder.

11. A device as claimed in claim 1, wherein there is a distribution bushing (10) which is mounted in said axial bore (7) in communication with the liquid ducts (8, 9) and in which said spray pin (11, 13) shifts under firm friction, and wherein the spray pin is formed from two pieces force-fitted in one another, one, forming the front part of the pin, being provided with the spray orifices, and the other (13), forming the rear part of the pin, being equipped with the shut-off piece (12), at least one axial groove (19) being provided between the two pieces, to allow the liquid to pass to the single-jet orifice (18).

12. An oral hygiene device comprising a nozzle-holder connectable to a liquid source and a nozzle removably attached to the nozzle-holder, the nozzle comprising a head having a series of holes forming outlet orifices of a first liquid duct and allowing emission of a multi-jet of liquid, and a single hole forming an outlet orifice of a second liquid duct and allowing emission of a single jet of liquid, a two-way valve being provided, controlled by a control member in order to direct the liquid either into the first duct or into the second duct, wherein the said valve (5, 40, 49, 57, 68, 76) and therefore branching of the two liquid ducts (8, 9, 62, 63) are located in the nozzle itself, and the valve is subjected to the action of a restoring spring (27, 48, 54, 64, 72, 85) which is such that the stable position of the device is for emitting the multi-jet of liquid, whilst under the action of an external force exerted on the control member counter to the action of the spring, the device emits the single-jet of liquid, the nozzle having a being equipped, at a lower end, with a retaining bushing (30) having a rear face, the rear face being inclined relative to the axis of the nozzle, and wherein there is a piece (4) for connection to the nozzle-holder, the corresponding face of which is inclined at the same angle relative to its axis, so that, in a relative position of the body (2) of the nozzle and of the connection piece (4), the two inclinations are compensated and the axes of the nozzle and of the connection piece coincide, whilst after a rotatio of one piece through 180° relative to the other, the inclinations are added and the axes of the nozzle and of the connection piece are inclined relative to one another at an angle equal to the sum of the two angles of inclination.

13. A device as claimed in claim 1, wherein the multi-jet outlet orifices (16a) in the nozzle head are arranged along a circle, and wherein the single-jet outlet orifice (18) is the center of the circle.

* * * * *